United States Patent
Yang et al.

(10) Patent No.: US 7,582,471 B2
(45) Date of Patent: Sep. 1, 2009

(54) BIOSENSOR FOR THE DETECTION OF PROTEIN KINASE A, AND KIT COMPRISING THE SAME

(75) Inventors: Eun-Gyeong Yang, Seoul (KR); Ki-Cheol Han, Seoul (KR); Dae-Sung Yoon, Kyunggido (KR); Tae-Song Kim, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 341 days.

(21) Appl. No.: 11/551,614

(22) Filed: Oct. 20, 2006

(65) Prior Publication Data

US 2008/0124790 A1     May 29, 2008

(30) Foreign Application Priority Data

Jul. 31, 2006    (KR)   ...................... 10-2006-0071996

(51) Int. Cl.
*C12M 1/34*      (2006.01)
(52) U.S. Cl. .................................. 435/287.1
(58) Field of Classification Search ........................ None
See application file for complete search history.

(56) References Cited

FOREIGN PATENT DOCUMENTS

| | | |
|---|---|---|
| JP | 10-293134 | 11/1998 |
| JP | 2004-125706 | 4/2004 |
| JP | 2004-511753 | 4/2004 |
| JP | 2005-502873 | 1/2005 |
| WO | WO-2005/038459 | 4/2005 |

OTHER PUBLICATIONS

Inamori et al. "Detection and quantification of on-chip phosphorylated peptides by surface plasmon resonance imaging techniques using a phosphate capture molecule", Anal. Chem. 2005, 77:3979-3985.*

* cited by examiner

*Primary Examiner*—Jon P Weber
*Assistant Examiner*—Bin Shen
(74) *Attorney, Agent, or Firm*—Joseph Hyosuk Kim; JHK Law

(57) ABSTRACT

The present invention relates to a biosensor specifically detecting a protein kinase A (PKA), and a diagnosis kit comprising the biosensor. In particular, the present invention relates to a biosensor for detecting a PKA comprising a cantilever, and a protein kinase inhibitor (PKI) immobilized on the surface of the cantilever; and a kit for diagnosing diseases caused by the increase of the activity of a protein kinase, comprising a sample, the biosensor, and a quantification manner.

13 Claims, 7 Drawing Sheets

SEQUENCE LISTING

<160> NUMBER OF SEQ ID NOS: 2

<210> SEQ ID NO 1
<211> LENGTH: 76
<212> TYPE: PRT
<213> ORGANISM: Artificial Sequence
<220> FEATURE:
<223> OTHER INFORMATION: Human Protein Kinse Inhibitor

<400> SEQUENCE: 1

```
Met Thr Asp Val Glu Thr Thr Tyr Ala Asp Phe Ile Ala Ser Gly Arg
 1               5                  10                  15

Thr Gly Arg Arg Asn Ala Ile His Asp Ile Leu Val Ser Ser Ala Ser
                20                  25                  30

Gly Asn Ser Asn Glu Leu Ala Leu Lys Leu Ala Gly Leu Asp Ile Asn
            35                  40                  45

Lys Thr Glu Gly Glu Glu Asp Ala Gln Arg Ser Ser Thr Glu Gln Ser
        50                  55                  60

Gly Glu Ala Gln Gly Glu Ala Ala Lys Ser Glu Ser
65                  70                  75
```

<210> SEQ ID NO 2
<211> LENGTH: 20
<212> TYPE: PRT
<213> ORGANISM: Artificial Sequence
<220> FEATURE:
<223> OTHER INFORMATION: Human PKI (5-24)

<400> SEQUENCE: 2

```
Thr Thr Tyr Ala Asp Phe Ile Ala Ser Gly Arg Thr Gly Arg Arg Asn
 1               5                  10                  15

Ala Ile His Asp
            20
```

BIOSENSOR FOR THE DETECTION OF PROTEIN KINASE A, AND KIT COMPRISING THE SAME

CROSS REFERENCE TO RELATED APPLICATION

This application claims priority to and the benefit of Korean Patent Application No. 10-2006-0071996 filed on Jul. 31, 2006, which is hereby incorporated by reference for all purposes as if fully set forth herein.

BACKGROUND OF THE INVENTION (a) Field of the Invention

The present invention relates to a biosensor specifically detecting protein kinase A (PKA), and a diagnosis kit comprising the biosensor. In particular, the present invention relates to a biosensor for detecting PKA comprising a cantilever, and a peptide derived from the protein kinase inhibitor (PKI) immobilized on the surface of the cantilever; and a kit for diagnosing diseases manifested by the increase of the activity of PKA, comprising a sample, the biosensor, and a quantification method.

(b) Description of the Related Art

Protein kinases play important roles in a variety of intracellular signaling pathways by catalyzing a reaction of a gamma-phosphoryl transfer from ATP to a hydroxyl group at serine, threonine or tyrosine residue of substrate proteins (H. C. Clevers, M. A. Oosterwegel, K. Georgopoulos, Immunol, Today 14 (1993) 592-597). The increase in the protein kinase activity is generally found in a variety of diseases, such as cancers, cardiovascular syndromes, immunological diseases, and hormonal disorders. Therefore, the protein kinases have been considered to be involved in the diseases mentioned above, and there have been extensive works to develop effective inhibitors specifically against thereto. In particular, protein kinase A (PKA) serves as a prototype for protein kinases since it is one of the best characterized members among the large family of protein kinases. In the absence of cAMP, PKA exists predominantly as an inactive tetrameric holoenzyme composed of two regulatory and two catalytic subunits. When the intracellular concentration of cAMP increases, cAMP binds to the regulatory subunits of the inactive PKA holoenzyme, leading to the decrease in the binding affinity between the regulatory and catalytic subunits. This results in the dissociation of two active catalytic subunits from the regulatory subunits to perform various phosphorylation reactions. In addition, the catalytic subunit of PKA can be potently inhibited by the physiological heat-stable inhibitor protein PKI, which may provide a second level of regulation. Based on the observation that certain cancer cells excrete the catalytic subunit of PKA out of cell, it was reported that the extracellular PKA catalytic subunit is correlated with cancers (Yee Sook Cho et al. PNAS 97(2) (2000) 835-840). Since the amount of such extracellular PKA catalytic subunit excreted from the cancel cell is minute, a highly selective detection tool is required for the quantitative and specific detection of the protein.

Various methods have been developed for measuring protein kinase activity. Such methods include a conventional radioactivity-based method that requires physical separation of substrate from its phosphorylated product, an enzyme linked immunosorbent assay (ELISA) that employs phosphospecific antibodies to capture product, and more recently developed fluorescence-based homogeneous nonradioactive assays based on fluorescence polarization (FP) and time-resolved fluorescence resonance energy transfer. Recent technological advances have aided development of numerous methodologies of monitoring interactions between peptides and proteins. In particular, the use of fluorescence polarization-based solution phase measurements and capillary electrophoresis (CE) has been well-established in studies for the peptide-protein binding. However, such direct method of quantitative analysis of an activated kinase is less sensitive than the methods based on signal amplifications by ELISA or an enzyme activity assay. Surface plasmon resonance (SPR) technology has also been recognized as an effective tool for biomolecular interaction analyses, despite the operation complexity. Accordingly, it is needed to develop a highly sensitive and convenient technique of detecting a peptide-protein binding.

SUMMARY OF THE INVENTION

In order to satisfy such need, the object of the present invention is to provide a biosensor for detecting protein kinase A (PKA) comprising a protein kinase inhibitor (PKI) peptide that specifically recognizes PKA. Another object of the present invention is to provide a kit for diagnosing PKA-associated diseases comprising the biosensor or bioarray for detecting PKA.

BRIEF DESCRIPTION OF THE DRAWINGS

FIG. 1A is a graph showing the result obtained by reacting 1 µM F-kemptide with 13.2 nM PKA in a reaction buffer containing 100 µM ATP at room temperature for 15 minutes, diluting F-kemptide to the concentration of 100 nM, and measuring fluorescence polarization in the presence of increasing concentrations of poly-Arg (●+PKA/○−PKA); and FIG. 1B is a graph showing the result of fluorescence polarization values measured in the presence of 5 µM poly-Arg as a function of time of the phosphorylation reaction by PKA.

FIG. 5A is a graph showing the results obtained by mixing 100 nM F-PKI-(5-24) peptide with varying concentrations of PKA of 13.2 nM (●), 66 nM (▲), and 132 nM (■) in the presence of increasing concentrations of ATP in a reaction buffer, and measuring the change in fluorescence polarization; and FIG. 5B is a graph showing the results obtained by mixing 100 nM F-PKI-(5-24) peptide with increasing concentrations of the catalytic subunit of PKA, and measuring the change in fluorescence polarization (♦+100 μM ATP/●−ATP).

FIG. 7A shows the results of the activity of PKA obtained by analyzing the phosphorylation of the substrate with increasing concentrations of PKA using ATP labeled with a radioisotope $^{32}P$. FIG. 7B shows the results of ELISA obtained by incubating varying concentrations of PKA in a 96-microwell plate on which a biotin-PKI-(5-24) peptide is immobilized, and detecting the captured PKA using a PKA specific antibody with enzyme attached. FIG. 7C is a graph showing the results obtained by incubating varying concentrations of PKA in a cantilever chip (5 cm×5 cm) consisting of 12 arrays (50 μm×150 μm) on which a biotin-PKI-(5-24) peptide is immobilized, and detecting the bound PKA by resonant frequency shift measurements (■+100 μM ATP/●−ATP).

DETAILED DESCRIPTION OF THE PREFERRED EMBODIMENTS

Figure 1A:
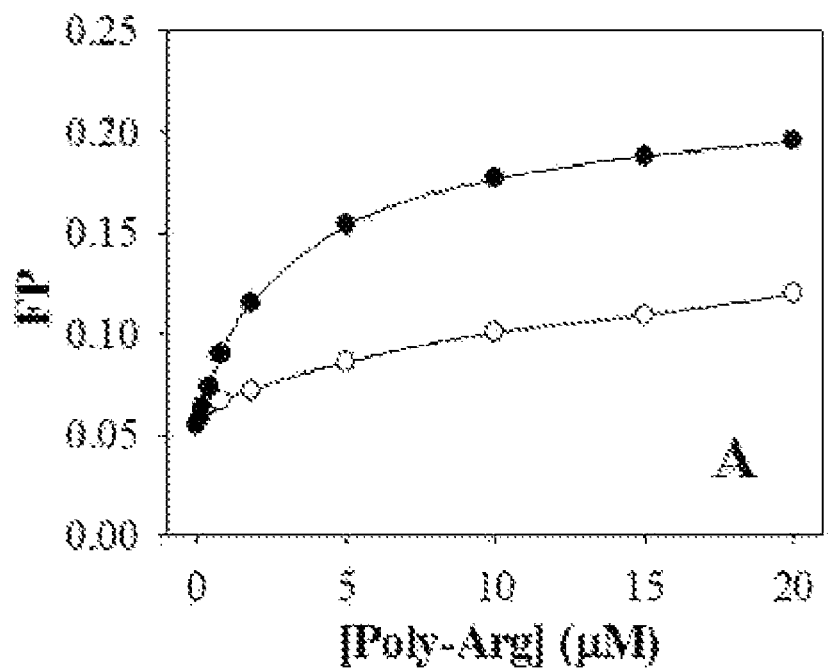
FIGS. 1A and 1B show the results of the activity of PKA measured by fluorescence polarization assay in the presence of poly-Arg according to Example 1.

A more complete appreciation of the invention, and many of the attendant advantages thereof, will be readily apparent as the same becomes better understood by reference to the following detailed description.

The present invention provides a technique to selectively detect a small amount of protein using a microcantilever sensor comprising a PKI (protein kinase inhibitor) peptide that specifically recognizes a catalytic subunit of PKA (protein kinase A).

Generally, when a protein kinase is activated, its activity can be analyzed by measuring an amplified signal from a phosphorylated product generated using an enzyme activity analyzing method. However, a direct analysis of the activated kinase is expected to provide clearer information on the enzyme condition and the kinase-mediated actions. Therefore, the present invention develops a nanobiosensor assay capable of directly analyzing activated PKA using a cantilever sensor that comprises a PKI peptide containing at least $5^{th}$ to $24^{th}$ amino acids of PKI that has a strong affinity to the catalytic subunit of PKA, thereby inhibiting the activity.

Specific detection of the catalytic subunit of PKA which is an activated form of the kinase generally reply on an assay using a radioactive isotope and an antibody to detect the kinase activity, a Western-blotting assay using an antibody that specifically recognizes PKA, and so on. However, such methods have some problems including the need to use harmful radioactive isotope and the low detection sensitivity.

To solve these problems, the present invention provides a sensor system based on a peptide ligand that specifically recognizes and binds to PKA. In particular, the present invention designs an analyzing method using a PKI peptide specifically recognizing the activated catalytic subunit of PKA, optimizes the conditions of the method, and provides a quantitative analysis method of specific protein-peptide binding. The method according to the present invention exhibits a higher sensitivity of at least about 100 times and a wider dynamic range than the activity assay using a radioactive isotope, due to the use of a PKI peptide immobilized on a cantilever surface to capture the catalytic subunit of PKA. Furthermore, the method according to the present invention is also much more sensitive than a direct binding assay based on fluorescence polarization and a signal-amplification method using an enzyme-attached antibody. According to the present invention, the catalytic subunit of PKA that is a marker molecule for a variety of disease conditions, such as cancer, cardiovascular syndromes, immunological diseases, and hormonal disorders, can be easily and specifically detected, thus the present invention has utility in diagnosis of the above diseases.

One of the objects of the present invention is to optimize the conditions for developing a PKA-detecting sensor based on a PKI peptide. For this purpose, in the present invention, magnetic beads, capillary electrophoresis, SPR, fluorescence polarization assay and the like were employed in testing the binding conditions between the catalytic subunit of PKA and the PKI peptide which is a binding ligand thereof, especially the effects of ATP and the concentration thereof. Further, in the present invention, a nanomechanical $Pb(Zr_{0.52}Ti_{0.48})O_3$ (PZT) cantilever is prepared, and the level of the binding between the catalytic subunit of PKA and the PKI peptide immobilized on the surface of the cantilever is measured in the presence or absence of ATP, thereby quantification of the catalytic subunit of PKA is successfully achieved using the obtained results.

Recently, microcantilever-based sensors have been emerged as excellent platforms for detecting extremely small forces, mechanical stresses and mass additions, thus offering promise of sensing specific biomolecular interactions with unprecedented sensitivity and dynamic range. While the earlier reports have demonstrated for detection of airborne components, more recent interest has shifted to detection of solution components by thin film on one side of the cantilever and by incorporating biomolecular recognition elements.

Generally, the cantilever can be used in detecting a binding with a specific material in both dynamic and static modes. The differences of surface stress in adsorption between the two opposite cantilever surfaces are measured in the static mode, which presents limitations such as a narrow dynamic range and parasitic defection. On the other hand, the dynamic mode is used to detect the resonance frequency shift caused by cantilever mechanical properties, such as changes of mass and stiffness in the binding surfaces. Due to its insensitive nature to the drift of deflection signal arising from the parasitic deflection, the dynamic detection method is considered as more advantageous. The present invention employs a cantilever with a dynamic mode detection to improve the detection sensitivity for a target material.

Accordingly, the present invention relates to a biosensor for detecting PKA comprising a cantilever, and a PKI peptide immobilized on the surface of the cantilever, and a kit for diagnosing diseases manifested by the increase of the activity of a protein kinase, comprising a sample, the biosensor or biosensor array for detecting PKA, and a quantification method.

In one aspect, the present invention relates to a biosensor for detecting PKA comprising a cantilever, and a PKI peptide immobilized on the surface of the cantilever.

The cantilever may have a width from 5 to 100 μm, and a length from 10 to 300 μm. When the size of the cantilever is larger than the above range, the detection limit becomes lowered. When the size of the cantilever is smaller than the above range, a high detection limit can be achieved, but there are some problems of poor reproducibility and many difficulties in fabrication thereof. Therefore, the above range of the size of the cantilever is preferable. The cantilever with the dynamic mode detection is preferable, and the membrane of the cantilever may be made of any material having a high elasticity, preferably one or more selected from the group consisting of silicon (Si), silicon nitride ($SiN_x$; x=1 to 1.5), silicon carbide (SiC), zirconia ($ZrO_2$) and alumina ($Al_2O_3$). In a preferable embodiment of the present invention, the cantilever may have the size of 50×150×2 μm (width×length×thickness), and may be made of a $SiN_x$/Si substrate that is prepared by depositing silicon nitride on the surface of Si wafer. Further, the surface of the cantilever may be properly modified. Such surface modification may be performed for the purpose of forming piezoelectric thin film for an active mode cantilever. The material for the surface modification is preferably Pb-based Perovskites oxide and/or zinc oxide (ZnO). The piezoelectric thin film may be formed by depositing $Pb(Zr_{0.52}Ti_{0.48})O_3$ on the surface via a dry process or wet process. In a preferable embodiment of the present invention, the cantilever may be a nanomechanical $Pb(Zr_{0.52}Ti_{0.48})O_3$ (PZT) cantilever wherein $Pb(Zr_{0.52}Ti_{0.48})O_3$ is deposited on the surface of the $SiN_x$/Si substrate.

In the present invention, the PKI peptide is a peptide that specifically binds to the catalytic subunit of PKA. As described above, PKA is a holoenzyme consisting of two regulatory subunits and two catalytic subunits. When the regulatory subunits and the catalytic subunits form a tetramer holoenzyme, PKA remains inactive, whereas when the catalytic subunits are dissociated from the regulatory subunits by cAMP to be a free form, PKA becomes activated. The PKI peptide is a peptide that specifically binds to the free catalytic subunit of PKA, and in the present invention, any mammal PKI may be used. Preferably, the PKI peptide used in the present invention may be a peptide derived from a human PKI (Accession No. AAB21141; mtdvettyad fiasgrtgrr naihdilvss asgnsnelal klagldinkt egeedaqrss teqsgeaqge aakses; SEQ ID NO: 1). The PKI peptide used in the present invention may be preferably a peptide having 20 to 76 amino acid residues comprising at least 20 amino acid residues from $5^{th}$ to $24^{th}$ positions of the PKI, wherein the 20 amino acid residues from $5^{th}$ to $24^{th}$ positions of the PKI play an important role in specific binding to the catalytic subunit of PKA. More preferably, the PKI peptide may be a peptide having the amino acid sequence of 'TTYADFIASGRTGRRNAIHD' (SEQ ID NO: 2), which is the sequence of the 20 amino acid residues from $5^{th}$ to $24^{th}$ positions of the PKI. Herein, the number of the amino acid is counted from the next amino acid following the methionine that is encoded by initiation codons.

The PKI peptide may be immobilized on the surface of the cantilever through any conventional chemical-coupling method. For example, biotin may be attached to the terminus of the PKI peptide to generate a biotin-labeled PKI, and streptavidin may be immobilized on the surface of the cantilever. Then, the biotin-labeled PKI peptide may be immobilized on the surface of the cantilever through the interaction between biotin attached to the PKI peptide and streptavidin immobilized on the surface. Alternatively, the surface of the cantilever may be coated with a material having an epoxy group, and the epoxy group may be reacted with the amine group of the PKI peptide, to immobilize the peptide on the surface of the cantilever. Besides, all chemical-coupling methods to immobilize the peptide to the surface of the cantilever may be employed, and such methods may be well known to the relevant field.

In the present invention, the binding between PKA and PKI may be analyzed by the change of resonance frequency. Therefore, the biosensor according to the present invention may further comprise a manner to measure the change of resonance frequency.

In the present invention, the biosensor may comprise two or more cantilevers on which the PKI peptide is immobilized, resulting in the formation of a bioarray type. In this case, the number of the cantilever may be properly controlled depending on the detection sensitivity and the kind of the sample to be analyzed, and generally, the number of the cantilever may be 3 to 12. Further, the interval between the cantilevers may be preferably 100 to 500 μm in order to obtain maximum detection sensitivity, but not essentially limited thereto. If the interval is narrower than the above range, interference may occur to affect detection, and if the interval is wider than the above range, the sensor size may become excessively large.

In another aspect, the present invention relates to a kit for diagnosing diseases manifested by the increase of the activity of PKA, comprising a sample, the biosensor or biosensor array for detecting PKA, and a quantification method.

In some diseases, such as cancers, cardiovascular syndromes, immunological diseases, and hormonal disorders, the increase of the activity of PKA is observed, and thus, these diseases may be diagnosed by analyzing the activity of PKA. The activity of PKA may be determined by the level of the free catalytic subunit which is an active form of PKA. The level of the free catalytic subunit may be measured by quantifying the binding with the PKI peptide that specifically binds thereto. Therefore, in the biosensor or bioarray according to the present invention, the diseases manifested by the activation of PKA may be easily and conveniently diagnosed by measuring the binding between the catalytic subunit of PKA and the PKI peptide immobilized in the biosensor or bioarray. The diseases diagnosed by determining the activation of PKA using the kit according to the present invention may include cancers, cardiovascular syndromes, immunological diseases, hormonal disorders, apoplexy, infectious diseases, and the like.

Since the catalytic subunit of PKA which is activated by dissociation from the regulatory subunit binds effectively to the PKI peptide in the presence of ATP (see Example 1 below), the diagnosing kit may further comprise ATP solution to increase the detection efficiency for the activated PKA. That is, the sample may be included with an ATP solution of a proper concentration, to yield effective binding of PKA present in the sample. In order to effectively bind PKA in the sample, the concentration of the ATP solution may be 10 to 1000 μM, and preferably, 10 to 500 μM.

The sample to be detected may be any cell or tissue obtained from a patient, and preferably, selected from the group consisting of all samples and secreted body fluid obtained by a minimal invasion, such as blood, plasma, and the like. The patient may be any mammals, and preferably human.

The detecting manner being comprised in the kit according to the present invention may include all apparatuses to measure the binding between PKA present in the sample and the PKI peptide immobilized on the biosensor. For example, the detecting manner may be an apparatus to measure the change of resonance frequency of the cantilever.

Still another aspect, the present invention provides a method of diagnosing diseases caused by the increase of the activity of protein kinase A, comprising the steps of:

contacting a sample obtained from a patient and a protein kinase inhibitor peptide having 20 to 76 amino acid residues comprising at least 20 amino acid residues from $5^{th}$ to $24^{th}$ amino acids of SEQ ID NO: 1; and detecting the interaction between the sample and the protein kinase inhibitor peptide.

In the method, the disease to be diagnosed may be selected from the group consisting of cancers, cardiovascular syndromes, immunological diseases, hormonal disorders, apoplexy, and infectious diseases. Therefore, the sample may be obtained from a patient suffering from the disease selected from the group consisting of cancers, cardiovascular syndromes, immunological diseases, hormonal disorders, apoplexy, and infectious diseases. Further, in the method, ATP solution having the concentration of 10 to 1000 μM may be added when contacting the sample and the protein kinase inhibitor peptide to stimulate the interaction therebetween.

The present invention is further explained in more detail with reference to the following examples. These examples, however, should not be interpreted as limiting the scope of the present invention in any manner.

EXAMPLE

In the following examples, the present inventors designed and performed an assay exhibiting a sensitivity of at least about 100 times higher than that of the conventional assay, on a PKI peptide-based PZT microcantilever sensor wherein the PKI peptide specifically recognizes the catalytic subunit of PKA. In the following examples, the binding between the catalytic subunit of PKA and the peptide ligand, PKI peptide, was analyzed through fluorescence polarization assay, capillary electrophoresis assay, SPR and ELISA, respectively. Further, the effect of ATP on the binding between the catalytic subunit of PKA and the PKI peptide was also analyzed.

Example 1

Inhibition of PKA Activity by PKI Peptide and Effect of ATP on PKA-PKI Binding 1.1. Analysis of PKA-PKI Binding by Measuring the Inhibition of the PKA Activity via Fluorescence Polarization-Based PKA Activity Measurements In this example, the kinase assay analyzing the kinase activity by measuring the increase of fluorescence polarization caused by a selective binding of a fluorescein-labeled substrate peptide to a polyamino acid when the substrate peptide is phosphorylated (J. Coffin, M. Latev, X. Bi, T. T. Nikiforov, Anal. Biochem. 278 (2000) 206-212) was employed, and its conditions were properly optimized. Generally, when the fluorescein-labeled substrate peptide designed to have the net charge of zero is phosphorylated by a kinase, the peptide becomes negatively charged and interacts electrostatically with a cationic polyamino acid, leading to change of fluorescence polarization. The kinase activity was analyzed by detecting such change of fluorescence polarization.

In order to optimize the conditions for analyzing the PKA activity, fluorescein-labeled kemptide (LRRASLG (SEQ ID NO:3); F-kemptide, Peptron Co. LTD., Korea) designed in such way that fluorescein was attached to the N-terminus of kemptide, and the total charge of the fluorescein-labeled kemptide was designed to be zero, was employed as a substrate of PKA. The fluorescein-labeled kemptide would become negatively charged when phosphorylated by PKA. F-kemptide (1 μM) was reacted with PKA in buffer solution (50 mM Hepes, pH 7.5, 5 mM $MgCl_2$, 1 mM DTT) in the presence of 100 μM ATP. Thereafter, the reaction solution was diluted with 50 mM Hepes buffer solution (pH 7.5) until the final concentration of F-kemptide reaches 0.1 μM, and fluorescence polarization was measured in the presence of increasing concentrations of poly-Arg (MW 75,000~150,000). Fluorescence polarization was measured on an LS-50B fluorescence spectrometer (Perkin Elmer, U.S.A.) with excitation at 488 nm and emission at 520 nm.

The obtained results are shown in FIG. 1A. As shown in FIG. 1A, the fluorescence polarization value of F-kemptide reacted with PKA increases with increasing concentrations of poly-Arg, while the unreacted (non-phosphorylated) F-kemptide shows no increase of the fluorescence polarization value. On the other hand, in the absence of poly-Arg, there is no significant difference between the fluorescence polarization values of the phosphorylated and non-phosphorylated substrates.

Figure 1B:
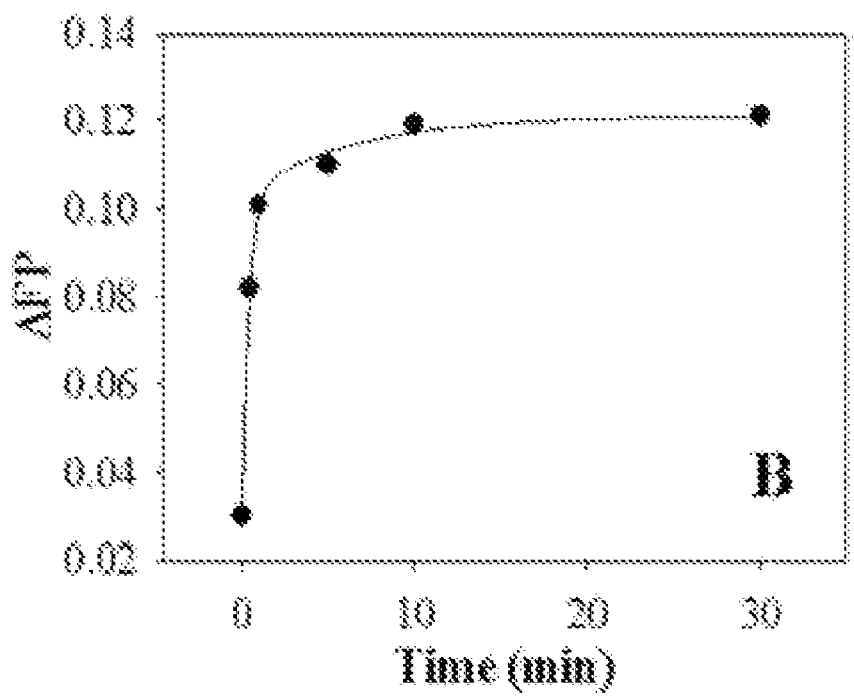

The optimal concentration of poly-Arg leading to the maximum difference between the fluorescence polarization values of the phosphorylated and non-phosphorylated substrates was determined as 5 μM, and the fluorescence polarization values were measured at the poly-Arg concentration of 5 μM for monitoring the time course of the PKA reaction. As a result, it was revealed that the fluorescence polarization value increases with time of reaction, eventually approaching to a plateau. The results are shown in FIG. 1B. The fluorescence polarization-based activity assay was then utilized for examining the inhibition of PKA by biotin-PKI-(5-24).

Figure 2:
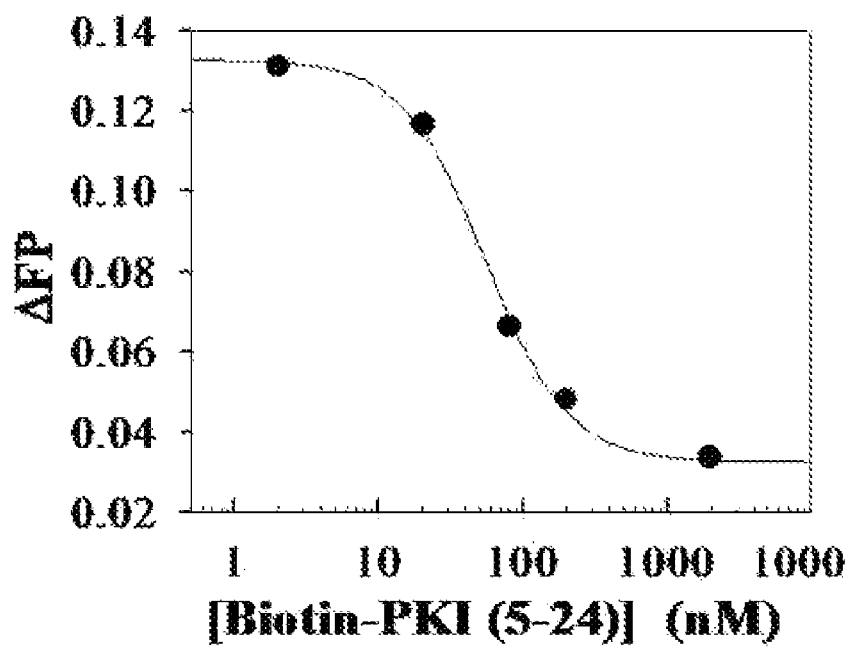
FIG. 2 is a graph showing the result of a quantitative analysis for inhibition of PKA by a biotin-PKI-(5-24) peptide using an activity assay in Example 1 (wherein 13.2 nM PKA and 1 µM F-kemptide are mixed and reacted for 15 minutes).

In addition, biotin-PKI-(5-24) (biotin-TTYADFIASGRT-GRRNAIHD: SEQ ID NO:2) (Peptron Co. LTD., Korea) having 20 amino acid residues from $5^{th}$ to $24^{th}$ positions of PKI and biotin at the N-terminus was synthesized and used in analyzing its inhibition of PKA using the fluorescence polarization-based activity assay. When 13.2 nM PKA and 1 μM F-kemptide were mixed and reacted in the presence of varying concentrations of biotin-PKI-(5-24) at room temperature for 15 minutes, the fluorescence polarization readout of the assay was found to decrease with increasing concentration of the PKI peptide with an $IC_{50}$ value of 54 nM (FIG. 2).

Next, attempts were made to capture PKA using biotin-PKI-(5-24) immobilized on streptavidin-coated magnetic beads (M-280 strabtavidin-coated magnetic beads, Dynal Biotech, Norway). Biotin-PKI-(5-24) was first immobilized on the streptavidin-coated magnetic beads through the biotin-streptavidin interaction, followed by addition of varying concentrations of the beads to buffer solution (50 mM Hepes, pH 7.5, 5 mM $MgCl_2$, 1 mM DTT) containing 13.2 nM PKA in the presence and absence of ATP, respectively, and incubation for 1 minute. The supernatant collected after removal of the beads was then assayed for the PKA activity. As a result, the presence of 400 μM ATP was at least partially effective in capturing the kinase on the beads, albeit much less than the free PKI-(5-24), indicating that ATP is likely to boost the protein-inhibitor binding. Consistent with these results, inhibition of PKA by PKI protein has been previously demonstrated to require the synergistic high-affinity binding of ATP (J. Lew, N. Coruh, I. Tsigelny, S. Garrod, S. S. Taylor, J. Biol. Chem. 272 (1997) 1507-1513).

1.2. Analysis of Effects of ATP on PKA-PKI Binding Using Capillary Electrophoresis and SPR F-PKI-(5-24) (Peptron Co. LTD., Korea) labeled with fluorescein at the N-terminus was synthesized and employed in analyzing effects of ATP on the PKA-PKI binding by capillary electrophoresis. Capillary electrophoresis was performed using P/ACE 5000 CE-LIF system (Beckman-Coulter, U.S.A.) equipped with fused-silica capillary (Polymicro, U.S.A.; length of 27 cm, inner diameter of 50 μm). Fluorescein was excited by a 488 nm line of a 3 mW Ar-ion laser attached to the system to emit fluorescence signals through a 520±10 nm filter, and the fluorescence signals were detected by an LIF detector. All solutions used in the analysis and capillary treatments were filtered through a filter having pore size of 0.2 μm. The capillary tubes were used after pretreating with 1 N NaOH and rinsing with deionized water for 5 minutes, respectively, and between runs, sequentially rinsed with 1 N NaOH, deionized water and buffer solution for 2 minutes each. Each sample was injected onto the capillary by pressure of 0.5 psi for 1 second, and separations were carried out by applying 10.8 kV. The buffer solution for electrophoresis contained 50 mM Hepes, pH 7.5, 1 M NDSB-195, 0.1% Triton X-100 and 10 mM DTT, and 5 mM $MgCl_2$ was further added to the PKA-PKI reaction solution.

Figure 3:
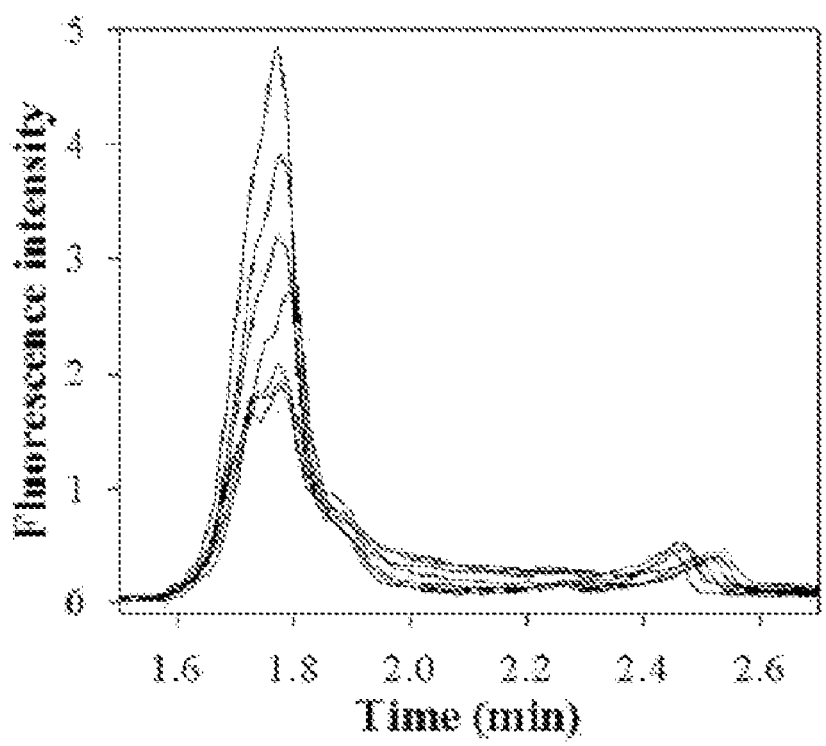
FIG. 3 is an electropherogram showing the result obtained by a capillary electrophoresis method to analyze the binding between 110 nM PKA and 50 nM F-PKI-(5-24) peptide with varying concentrations of ATP as 0, 0.025, 0.1, 1, 10, 500 µM. The highest peak corresponds to the electropherogram for the case of F-PKI-(5-24) only without PKA.

Since inclusion of 1 M NDSB-195 and 0.1% Triton X-100 in the running buffer had been reported to help reduction of peptide adsorption to a glass surface, such mixture solution was used to obtain reproducible peptide peaks. The results are shown in FIG. 3. As shown in FIG. 3, when PKA was added to the F-PKI-(5-24) containing solution without ATP, a little decrease in the peak was observed in capillary electrophoresis analyses. In contrast, addition of ATP yielded a concentration-dependent decrease of the peptide peak, although the complex peak was not visible. Such result indirectly demonstrates that ATP contributes to the formation of the complex between F-PKI-(5-24) and PKA. On the other hand, no significant change in the peak was observed for the F-PKI-(5-24) peptide without PKA in the presence of 500 μM ATP.

The effect of ATP on the PKA-PKI binding was also evaluated using an SPR analyzer, Biacore 3000 biosensor system (Biacore, U.S.A.). The surface of a CM5 sensor chip (Biacore, Applied Biosystems, U.S.A.) was activated with N-ethyl-N'-(3-dimethylaminopropyl)carbodiimide (EDC) and N-hydroxysuccinimide (NHS), and 50 μg/mL streptavidin was applied thereto, to immobilize on the surface of sensor via an amine-coupling method. Biotin-PKI-(5-24) was then applied to the streptavidin immobilized sensor surface at the rate of 5 μM/min for 100 seconds, to form the biotin-streptavidin binding. The mixture solutions of 132 nM PKA and varying concentrations of ATP were applied at the rate of 30 μM/min for 100 seconds, and the buffer solution was then applied for 200 seconds, to obtain sensorgrams. The results are shown in FIG. 4.

Figure 4:
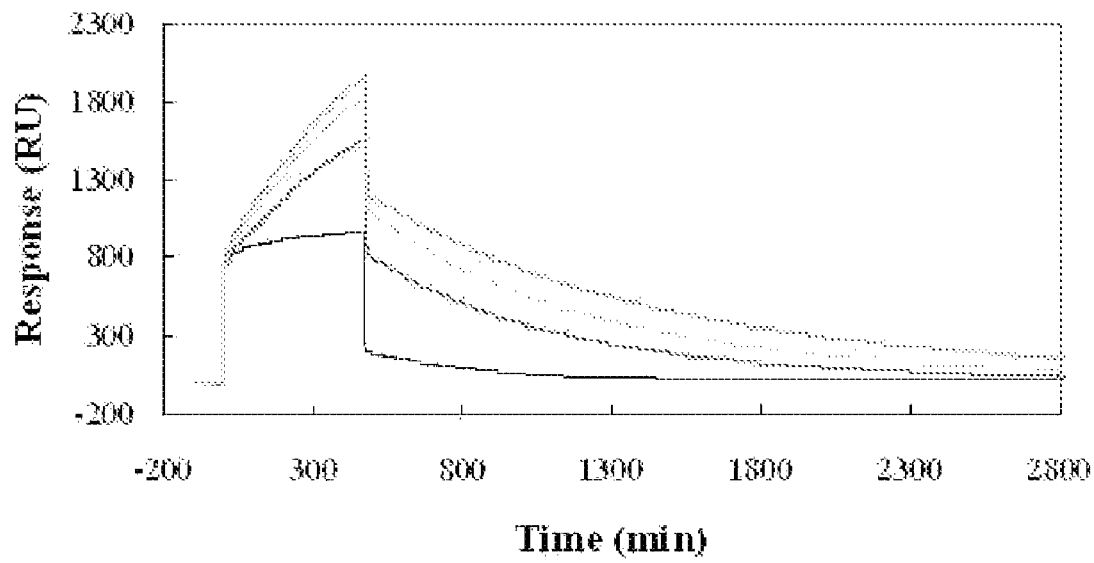
FIG. 4 is a sensorgram showing the results obtained by SPR analysis for the binding between PKA and biotin-PKI-(5-24) peptide, using a Biacore CM5 biosensor on which the biotin-PKI-(5-24) peptide was immobilized through the biotin-streptavidin interaction, followed by passing the PKA-containing solutions premixed with varying concentrations of ATP at 1, 5, 10, 50, 100 µM onto the PKI peptide-bound chip and a reference chip (which is a chip on which only streptavidin is attached), respectively, and subtracting the response of the reference chip from that of the PKI peptide-bound chip.

As shown in FIG. 4, it was confirmed that the concentration of ATP has an effect on the interaction between PKA and biotin-PKI-(5-24) immobilized on the sensor surface. While the on-rate of PKA increased with increasing concentrations of ATP, PKA dissociated from the peptide inhibitor on the sensor surface more slowly at higher ATP concentrations. When a similar test was performed using weakly binding biotin-Ala-kemptide (biotin-LRRAALG (SEQ ID NO:4) ) with the affinity for PKA of 10 μM, binding of PKA was not observed even at the highest ATP concentration applied.

1.3. Analysis of the PKA-PKI Binding by Fluorescence Polarization Measurements

Figure 5A:
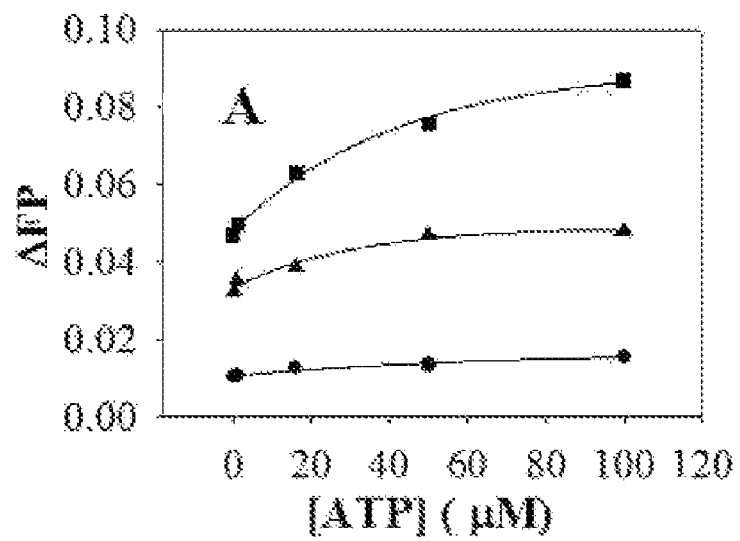
FIGS. 5A and 5B show the results analyzed by homogeneous fluorescence polarization assay for the binding between PKA and F-PKI-(5-24) peptide at room temperature.
Figure 5B:
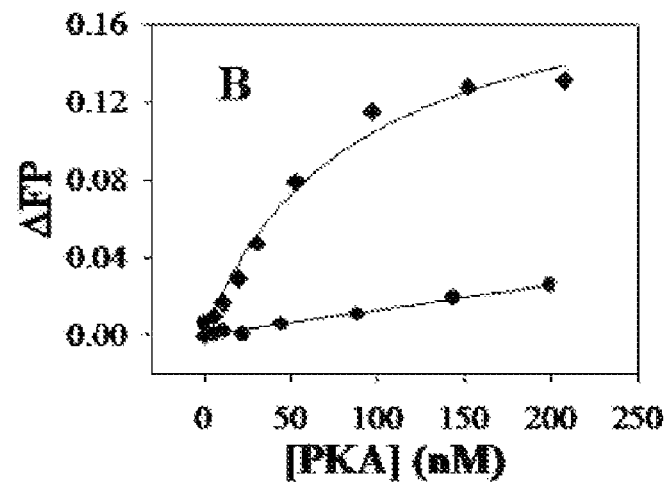

In order to directly confirm the PKA-PKI binding, the fluorescence polarization value was measured for F-PKI-(5-24) by the same method as described in Example 1, and the results are shown in FIG. 5A. As shown in FIG. 5A, the fluorescence polarization values increase with increasing concentrations of ATP, and leveled off, with respect to each of 13.2 nM, 66 nM, and 132 nM PKA. In addition, 100 nM F-PKI-(5-24) was mixed with the buffer solution (50 mM Hepes, pH 7.5, 5 mM $MgCl_2$, 1 mM DTT), and the fluorescence polarization values were measured with varying concentrations of PKA. The results are shown in FIG. 5B. As shown in FIG. 5B, the fluorescence polarization values increase linearly up to 53 nM PKA in the presence of 100 μM ATP, while in the absence of ATP, only slight change is observed in the fluorescence polarization.

EXAMPLE 2

Analysis Using a Microcantilever

A PZT nanochemical cantilever sensor array composed of smart piezoelectric material was fabricated and used as a biosensor since the electrical measurement of the signal presents a convenient method compared to the measurement with an external oscillator.

The substrates were prepared by depositing 1.2 μm thick low-stress silicon nitride on 100 mm diameter p-doped Si (100) wafers with low-pressure chemical vapor deposition (LPCVD). The bottom electrode of Pt/Ta thin film was prepared on the silicon-nitride/silicon substrates by RF magnetron sputtering, followed by deposition of the PZT thin film of 0.5 μm on the substrate by a diol-based sol-gel route. For the metal-ferroelectric-metal capacitor structure, DC sputtering was used to deposit a Pt layer for the top electrode.

After ion milling to etch the Pt for the top electrode, inductively coupled plasma was utilized to etch the PZT for the piezoelectric material. The Pt bottom electrode was also patterned by ion milling, and the bottom silicon nitride window was patterned by a reactive ion etching, followed by wet etching of the bulk silicon with a KOH silicon etchant. Finally, the cantilever was formed by silicon nitride etching with reactive ion etching, and a $SiO_2$ thin film was deposited for the electrical and chemical passivation layer. The biosensor fabricated in this example was designed to contain 3 or 12 cantilever arrays, and the dimension of each cantilever was 50 μm×150 μm.

Figure 6A:
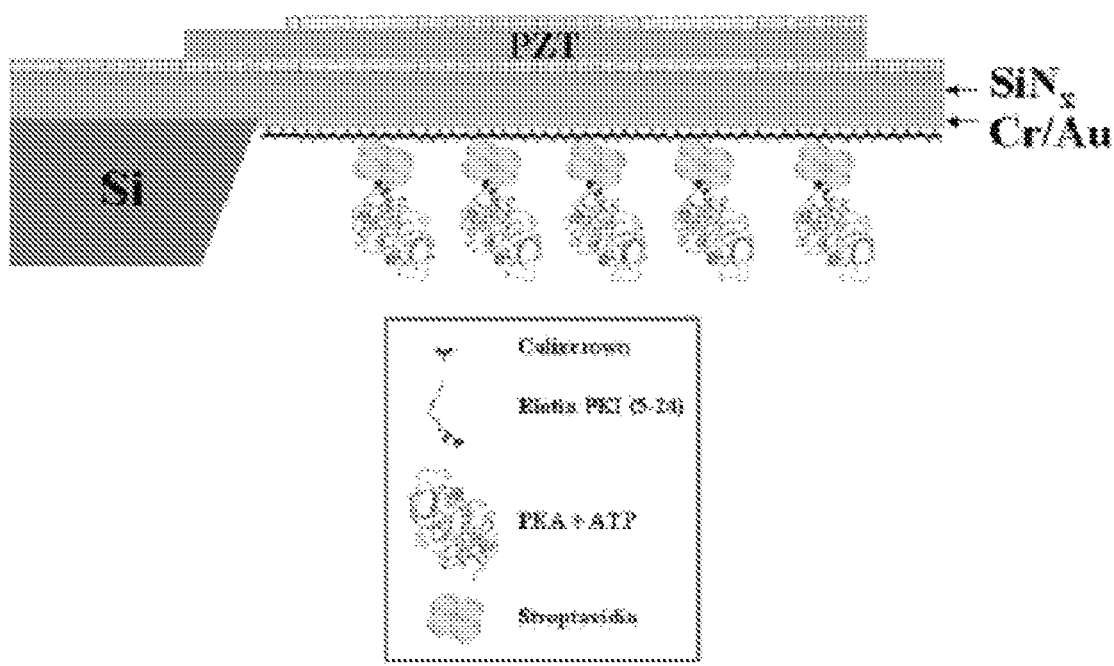
FIG. 6A is a schematic of a sensor assay wherein Calix-crown SAM (self-assembled monolayer), streptavidin, and a biotin-PKI-(5-24) peptide are sequentially immobilized on the Au surface of PZT cantilever, and the catalytic subunit of PKA in complex with ATP is then captured.

For the PKA binding assay, the surface of the cantilever fabricated as above was functionalized as below. The fabricated cantilever is schematically shown in FIG. 6A.

Figure 6B:
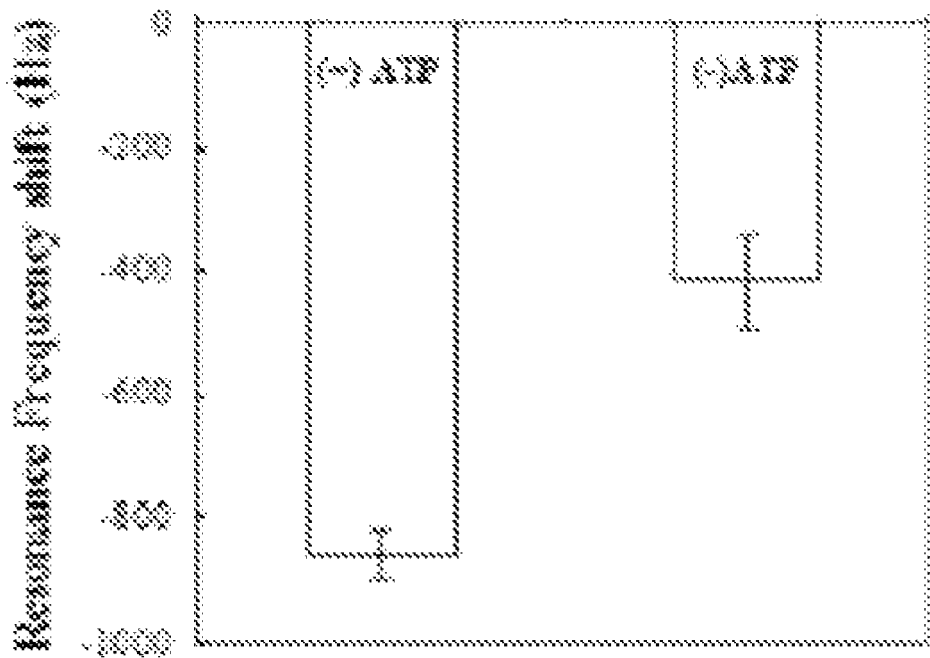
FIG. 6B is a graph showing the results obtained by measuring the resonant frequency shifts upon incubation with 132 nM PKA on the cantilever chips (5 cm×5 cm) consisting of 3 arrays (50 μm×150 μm) (+/−100 μM ATP).

First, a Cr (10 nm)/Au (50 nm) layer was deposited on the bottom silicon nitride side of the nanochemical PZT cantilever using an e-beam evaporator. The PZT nanomechanical cantilever was then cleaned in $H_2O_2:H_2SO_4$ (1:4 vol/vol) and subsequently rinsed in deionized water. Streptavidin was immobilized on the cleaned surface of the cantilever using calixcrown (a calixarene derivative) self-assembled monolayers (SAMs) which have an efficient immobilization property owing to their recognition of ammonium ions of proteins (Y. Lee, E. K. Lee, Y. W. Cho, T. Matsui, I.-C. Kang, T.-S. Kim, M. H. Han, Proteomics 3 (2003) 2289-2304). After treated with 10 μg/ml streptavidin in PBS at room temperature for 1 hour, the cantilever was washed with 30 ml of PBST (PBS with 0.5% Tween 20, pH 7.5) and then dried under nitrogen gas. In order to minimize non-specific binding, the cantilever was immersed in PBS containing 5% BSA at room temperature for one hour, and washed with PBST. Then the washed cantilever was treated with PBS buffer solution containing 200 nM biotin-PKI-(5-24) at room temperature for one hour, washed with 30 ml of PBST, and then dried under nitrogen gas. The biotin-PKI-(5-24) immobilized cantilever was treated with PKA (in 50 mM Hepes, pH 7.5, 5 mM $MgCl_2$, 1 mM DTT) at room temperature for 30 minutes, and washed with buffer solution (50 mM Hepes, pH 7.5, 5 mM $MgCl_2$, 1 mM DTT). Then, the resonance frequency of the cantilever was measured by a precision impedance analyzer (4294A, Agilent technologies, U.S.A.), and the results are shown in FIG. 6B.

Figure 7A:
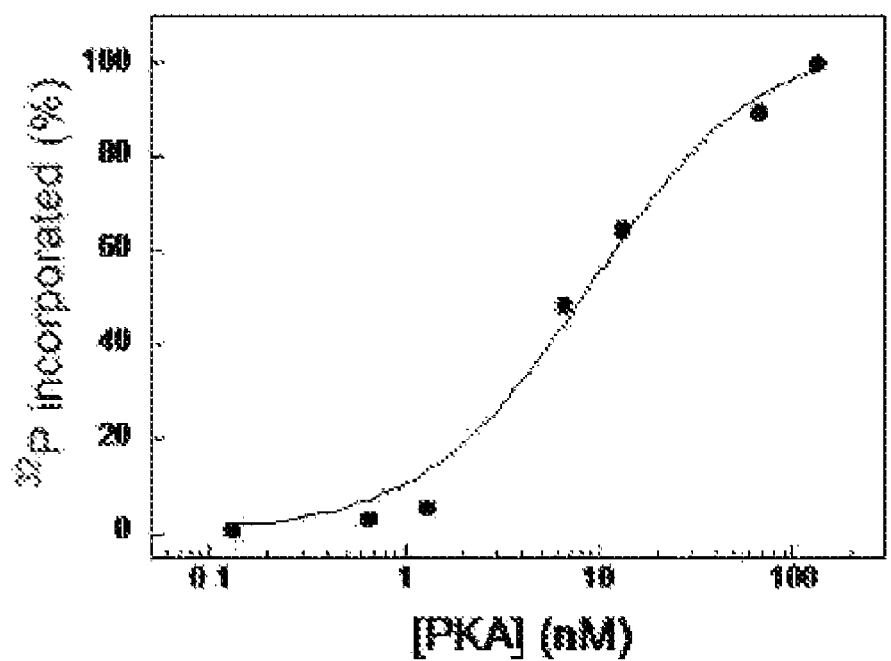
FIGS. 7A to 7C are the graphs comparing the present invention with the conventional quantitative analyses of PKA.

After immobilization of streptavidin on the cantilever surface modified with Calixcrown SAMs, followed by binding of biotin-PKI-(5-24) thereto, the effect of ATP on the PKI-PKA binding was tested by treating with 132 nM PKA in reaction buffer in the presence or absence of ATP. For the quantification of the PKA-PKI binding, a cantilever array sensor consisting of 3 cantilevers having the same size (50 μm×150 μm) was used. The resonant frequency of the treated cantilever was repeatedly measured until it reached a saturated value, and subtracted from the frequency of the negative control cantilever to remove the error generated from nonspecific binding as well as the conditions of the measuring environment. As shown in FIG. 6B, the sensors treated with PKA with ATP caused a more negative resonant frequency change, and the difference in the resonance frequency between the samples with and without ATP was more than 300 Hz with the cantilever arrays, demonstrating that ATP assists the PKA-PKI binding. Then, the quantitative aspect of such binding was explored. As shown in FIG. 7C, the magnitude of the resonant frequency change increased with increasing concentrations of PKA catalytic subunit in the presence of ATP. The sensitivity limit for detecting activated PKA in the presence of ATP was <10 μM. On the other hand, the increase of the resonant frequency shift was minimal in the absence of ATP. Accordingly, a simple and direct sensor system comprising microcantilever(s) and peptide specific to the catalytic subunit of PKA can be provided for detecting activated PKA. In addition, such a peptide-based cantilever sensor may be useful in diagnosis of cancer and the like, considering that activated PKA has been found to be released from certain carcinoma cell lines.

COMPARATIVE EXAMPLE 1

Activity Assay Using $^{32}$P-ATP

In order to compare with the analysis of PKA activity using the cantilever sensor according to the present invention, a conventional activity assay for PKA activity using a radioisotope was conducted. Kemptide (10 μM) was employed as a substrate peptide for PKA, and reacted in buffer solution (50 mM Hepes, pH 7.5, 5 mM $MgCl_2$, 1 mM DTT) in the presence of 50 μM of ATP containing $^{32}$P-ATP (5 μCi) with varying concentrations of the catalytic subunit of PKA at 50 μL volume per a sample for 15 minutes. 10 μL of 30% (v/v) phosphoric acid was then added to the reaction sample to stop the reaction. Thereafter, for quantification of the radioactivity of the phosphorylated kemptide, 40 μL of the stopped reaction sample was processed by spotting on P81 phosphocellulose paper, and sufficiently washed with excess deionized water for 3 hours at least 5 times to remove unreacted $^{32}$P-ATP. Then the P81 paper was dried, and the radioactivity was quantified using Phospho-imager (BAS $^{32}$P-image analyzer, FUJIFILM Life Science). The obtained results are shown in FIG. 7A. As shown in FIG. 7A, it can be confirmed that the activity assay can be conducted at the concentration of PKA of at least 1 nM or higher.

COMPARATIVE EXAMPLE 2

Analysis Using Enzyme-Linked ImmunoSorbent Assay (ELISA)

In order to compare with the analysis of PKA activity using the cantilever sensor according to the present invention, another conventional assay for the PKA-PKI binding using ELISA wherein the signal is amplified by an enzyme attached to an antibody was conducted. The biotin-PKI-(5-24) peptide was immobilized to microwells of 96-well plate precoated with a streptavidin in PBST buffer solution (10 mM $Na_2HPO_4$, 2 mM $KH_2PO_4$, 2.7 mM KCl, 137 mM NaCl, 0.5% Tween-20, pH 7.4) via the biotin-streptavidin interaction, followed by addition of PBST containing 5 mM $MgCl_2$ and 200 μM ATP with varying concentrations of the catalytic subunit of PKA, and then, incubated for one hour. Such treated microwells were washed three times with 300 μL of PBST containing 5 mM $MgCl_2$ and 200 μM ATP. Mouse monoclonal antibody (abcam, UK) was diluted with PBST containing 5 mM $MgCl_2$ and 200 μM ATP by 1/500. Then, 100 μL of the diluted antibody was added to the washed microwells, and incubated at room temperature for 1 hour.

Thereafter, the resulting microwells were washed three times with 300 μL of PBST containing 5 mM $MgCl_2$ and 200 μM ATP. HRP (horse-radish peroxidase)-attached antibody (rabbit anti-mouse IgG-HRP, abcam, UK) which is a secondary antibody recognizing the monoclonal antibody was diluted with PBST containing 5 mM $MgCl_2$ and 200 μM ATP by 1/500. Then, 100 μL of the diluted antibody was added to the washed microwells, and incubated for 1 hour. After washing three times with 300 μL of PBST containing 5 mM $MgCl_2$ and 200 μM ATP, 100 μL of TMB (3,3,5,5-tetramethylbenzidine, GenDEPOT, USA) which is a substrate of HRP was added, and reacted for 30 minutes. Then, 100 μL of TMB stop buffer (GenDEPOT, USA) was added to terminate the reaction and the absorbance was measured at 450 nm.

Figure 7B:
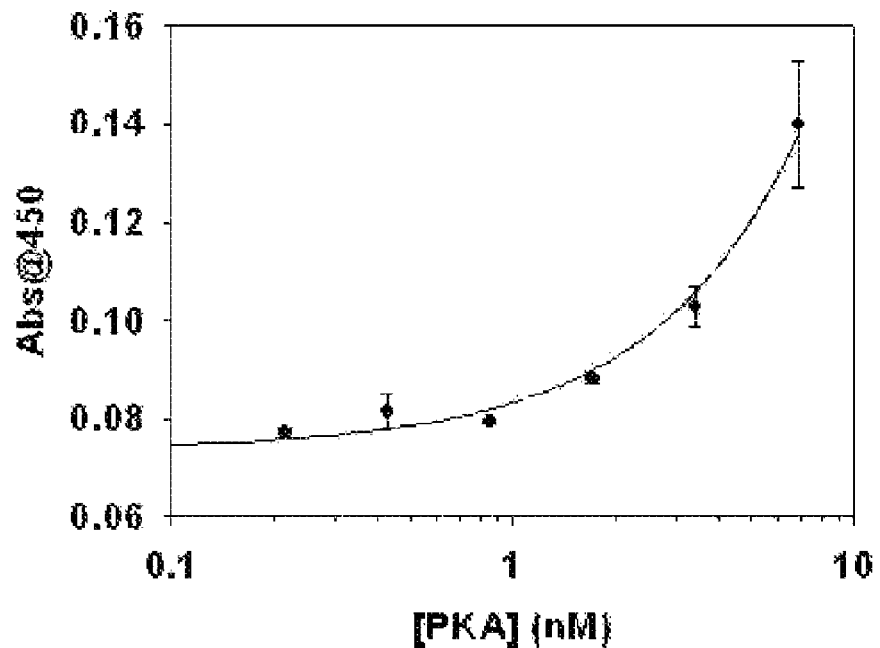
Figure 7C:
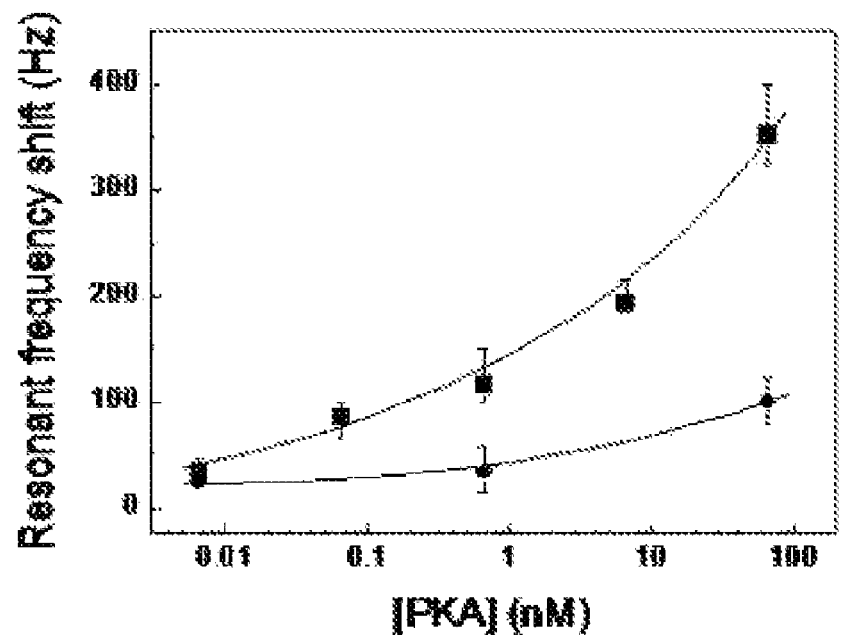

The obtained results are shown in FIG. 7B. As shown in FIG. 7B, it can be confirmed that the signal can be detected by measuring the change of absorbance at the concentration of PKA of at least 1 nM or higher.

Results

Figure 8:
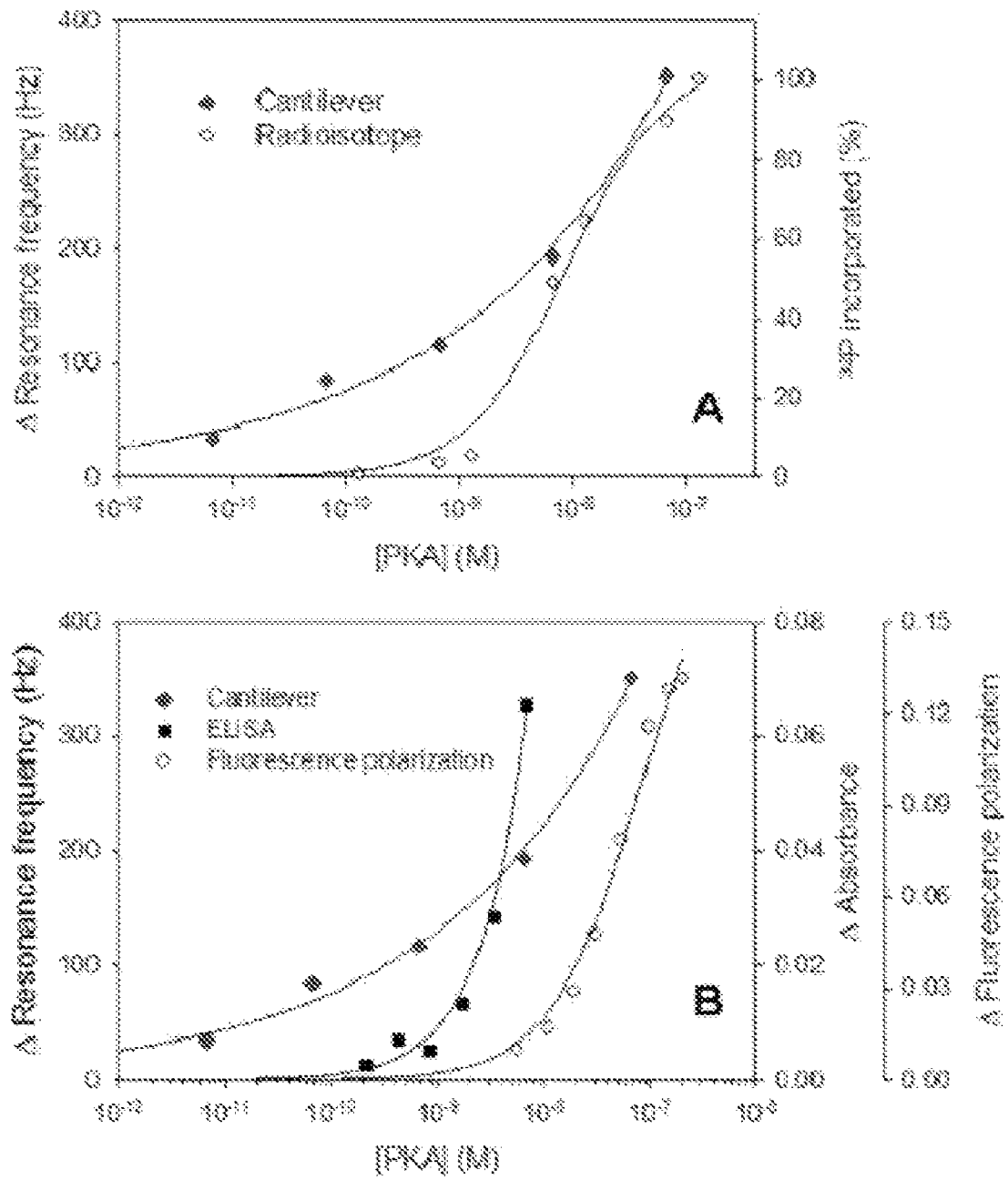
FIG. 8 shows the comparison of the present invention with other assays, wherein A is a graph wherein the results of the present invention as shown in FIG. 7C are plotted together with the results of radioisotope-based activity assay as shown in FIGS. 7A, and B is a graph wherein the results of the present invention as shown in FIG. 7C are plotted together with the results obtained by directly analyzing the binding using fluorescence polarization as shown in FIG. 5B and by using ELISA capable of amplifying the signal by the enzyme attached to the antibody as shown in FIG. 7B.

The comparison of the analysis results obtained from the cantilever according to the present invention with the results obtained by Comparative examples 1 and 2, and a homogeneous fluorescence polarization assay are shown in FIG. 8. As shown in FIG. 8, it is revealed that the assay according to the present invention wherein a PKI peptide is immobilized on the surface of the cantilever and the binding between the catalytic subunit of PKA and the PKI peptide is analyzed by measuring the resonance frequency exhibits a higher sensitivity by 2 orders of magnitude and a wider dynamic range than the activity assay using a radioactive isotope or the ELISA method based on signal amplification using an antibody with enzyme attached, and exhibits a higher sensitivity by 3 orders of magnitude than the direct fluorescence polarization assay. In conclusion, the sensor system according to the present invention is simple and convenient due to the simple combination of microcantilever(s) and the catalytic subunit of PKA; thereby a simple and convenient quantification can be achieved without secondary signal amplification even when a minute amount of the catalytic subunit of PKA exists; therefore can be used in diagnosis of cancer and the like by detecting the catalytic subunit of PKA.

As described above, the present invention provides a quantification technique using a PZT microcantilever sensor based on a PKI derived peptide specifically binding to PKA, which can detect the catalytic subunit of PKA that is a marker molecule of cancer, to a higher sensitivity of at least about 100 times than the conventional methods; therefore useful in diagnosis of cancer and the like requiring the highly sensitive detection of very small amount of PKA.

What is claimed is:

1. A biosensor for detecting protein kinase A comprising a cantilever, and a protein kinase inhibitor peptide having 20 to 76 amino acid residues comprising at least 20 amino acid residues from $5^{th}$ to $24^{th}$ amino acids of SEQ ID NO: 1 immobilized on the cantilever.

2. The biosensor according to claim 1, wherein the protein kinase inhibitor peptide has the amino acid sequence of SEQ ID NO: 1.

3. The biosensor according to claim 1, wherein the protein kinase inhibitor peptide has the amino acid sequence of SEQ ID NO: 2.

4. The biosensor according to claim 1, wherein the cantilever has a breath from 5 to 100 μm and a length from 10 to 300 μm, and comprises a membrane made of one or more selected from the group consisting of silicon (Si), silicon nitride ($SiN_x$; x=1 to 1.5), silicon carbide (SiC), zirconia ($ZrO_2$) and alumina ($Al_2O_3$).

5. The biosensor according to claim 4, wherein the surface of the cantilever is modified with one or more selected from the group consisting of a Pb-based Perovskites oxide and zinc oxide (ZnO).

6. The biosensor according to claim 5, wherein the cantilever is a $Pb(Zr_{0.52}Ti_{0.48})O_3$ (PZT) cantilever prepared by depositing $Pb(Zr_{0.52}Ti_{0.48})O_3$ on the surface of a $SiN_x$/Si (x=1 to 1.5) substrate.

7. The biosensor according to claim 1, wherein streptavidin is fixed on the surface of the cantilever, biotin is bound to N-terminus of the protein kinase inhibitor peptide, and streptavidin and biotin are reacted with each other, to immobilize the protein kinase inhibitor peptide on the surface of the cantilever.

8. The biosensor according to claim 1, further comprising a manner to measure the change of resonance frequency.

9. The biosensor according to claim 1, further comprising one or more cantilevers wherein the protein kinase inhibitor peptide is immobilized on the surface of each cantilever.

10. The biosensor according to claim 9, wherein the interval between of the cantilevers is 100 to 500 μm.

11. A kit for diagnosing diseases caused by the increase of the activity of protein kinase A, comprising: one or more biosensors of claim 1; and instruction for use.

12. The kit according to 11, wherein the disease is selected from the group consisting of cancers, cardiovascular syndromes, immunological diseases, hormonal disorders, apoplexy, and infectious diseases.

13. The kit according to 11, further comprising ATP solution having the concentration of 10 to 1000 μM.

* * * * *